United States Patent [19]

Cherry et al.

[11] Patent Number: 4,769,367
[45] Date of Patent: Sep. 6, 1988

[54] HETEROCYCLIC AMINO COMPOUNDS

[75] Inventors: Peter C. Cherry, South Harrow; Adrian J. Pipe, Greenford; John Kitchin, Pinner; Alan D. Borthwick, London; Richard J. Coles, Uxbridge; Derek Burn, Chalfont St. Giles, all of England

[73] Assignee: Glaxo Group Limited, London, England

[21] Appl. No.: 878,263

[22] Filed: Jun. 25, 1986

Related U.S. Application Data

[63] Continuation-in-part of Ser. No. 726,663, Apr. 24, 1985, abandoned.

[30] Foreign Application Priority Data

Apr. 24, 1984 [GB] United Kingdom ............ 8410459
Oct. 23, 1985 [GB] United Kingdom ............ 8526210

[51] Int. Cl.$^4$ .................... A61K 31/55; A61K 31/40; C07D 209/56
[52] U.S. Cl. ............................ 514/217; 514/411; 548/430
[58] Field of Search ............... 548/430; 514/411, 217

[56] References Cited

U.S. PATENT DOCUMENTS 4,385,056  5/1983  Loozen ..................... 514/411
4,496,579  1/1985  Crane et al. ............... 514/411
4,680,411  7/1987  Picart ....................... 548/430

OTHER PUBLICATIONS

Derwent Abstract No. 56634V.
Derwent Abstract No. 48894V.
Derwent Abstract No. 48895V.

Primary Examiner—Mary E. Ceperley
Attorney, Agent, or Firm—Morgan & Finnegan

[57] ABSTRACT

Compounds of the general formula (I)

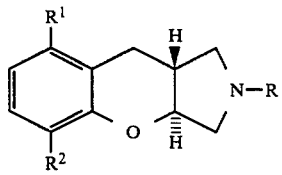

(wherein R is H, alkyl, alkenyl, alkynyl, cycloalkyl, aralkyl or CHO; and $R^1$ and $R^2$ each represents H, fluorine or chlorine);

and their salts have selective $\alpha_2$-adrenoreceptor antagonist action.

The compounds may be prepared by amination of compounds of the general formula (II):

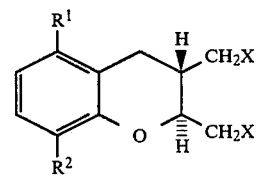

(wherein X is a leaving group).

9 Claims, No Drawings

HETEROCYCLIC AMINO COMPOUNDS

This is a continuation-in-part application of copending U.S. application Ser. No. 726,663, filed on 4/24/85, now abandoned.

This invention relates to heterocyclic amino compounds. More specifically this invention relates to novel benzopyranopyrrole derivatives, to processes for the preparation thereof, to pharmaceutical preparations containing them, and to their use in medicine.

The alpha ($\alpha$)-adrenoreceptors of the sympathetic nervous system are classified pharmacologically into two sub-groups, namely $\alpha_1$ and $\alpha_2$. The $\alpha_2$-type are situated predominantly on the presynaptic terminals of noradrenergic neurones and are activated by the released neurotransmitter. Such activation results in a diminished release of noradrenaline on subsequent stimulation of the neurones, the $\alpha_2$-adrenoreceptors thus forming part of an autoinhibitory feedback mechanism for regulating the synaptic concentration of the neurotransmitter. A selective $\alpha_2$-adrenoreceptor antagonist would be expected to produce an increase in the synaptic concentrations of noradrenaline by blocking the autoinhibitory feedback mechanism and would thus be of potential value in human medicine for the treatment of disorders such as depression which are associated with a deficiency of noradrenaline at postsynaptic adrenoreceptors.

$\alpha_2$-Adrenoreceptors also occur at non-neuronal sites such as on blood-platelets, in pancreatic islet cells, on adipocytes and in the proximal tubules of the kidney. Activation of $\alpha_2$-adrenoreceptors at these sites leads to platelet aggregation, inhibition of insulin release, inhibition of lipolysis and retention of sodium respectively.

A selective $\alpha_2$-adrenoreceptor antagonist thus has a potential therapeutic use as an antidepressant either alone or in a complimentary combination with an established antidepressant, and in either treating or preventing conditions such as migraine, thrombosis, diabetes, obesity, hypertension, constipation, paralytic ileus and senile dementia.

We have now found that the compounds of formula (I) below and their physiologically acceptable salts have a selective $\alpha_2$-adrenoreceptor antagonist action.

The invention thus provides compounds of general formula (I)

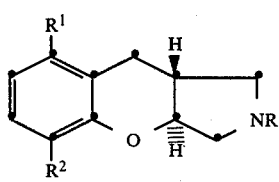

wherein
R is a hydrogen atom or a group selected from $C_{1-6}$ alkyl (optionally substituted by $C_{3-7}$ cycloalkyl), $C_{3-6}$ alkenyl, $C_{3-6}$ alkynyl, $C_{3-7}$ cycloalkyl, aralkyl (in which the alkyl moiety contains 1–5 carbon atoms), and —CHO; and $R^1$ and $R^2$, which may be the same or different, each represent a hydrogen atom or a fluorine or chlorine atom; and the physiologically acceptable salts thereof.

In general formula (I), the alkyl, alkenyl and alkynyl groups represented by R may be straight or branched chain groups.

When R contains a —C=C— or —C≡C— linkage this is not directly attached to the nitrogen atom. When R is alkyl it may be, for example, methyl, ethyl or propyl, methyl being preferred. When R is an alkyl group substituted by a $C_{3-7}$ cycloalkyl group it may be, for example, cyclopropyl $C_{1-3}$ alkyl such as cyclopropylmethyl. When R is alkenyl it may be, for example, allyl and when R is alkynyl it may be, for example, propynyl. When R is cycloalkyl it may be, for example, cyclopropyl. When R is an aralkyl group it may be, for example, phen$C_{1-5}$alkyl, such as benzyl.

Suitable physiologically acceptable salts are the acid addition salts formed with inorganic acids, for example hydrochlorides, hydrobromides, phosphates and sulphates, and with organic acids, for example citrates, tartrates, acetates, maleates and succinates. The hydrochlorides are particularly useful.

It will be appreciated that each compound of general formula (I) is a trans isomer andd exists as two enantiomers. The structural formula herein are to be understood to depict either enantiomer of each compound concerned as well as mixtures of the enantiomers, including racemates, even though the precise structure as set out only relates to one enantiomer.

A preferred group of compounds of general formula (I) is that wherein R is a hydrogen atom. Another preferred group of compounds of general formula (I) is that wherein R is a $C_{1-3}$ alkyl group, particularly a methyl or ethyl group.

A further preferred group of compounds of general formula (I) is that wherein $R^1$ and/or $R^2$ represent a fluorine atom.

Important compounds are ($\pm$)-trans-5-fluoro-1,2,3,3a,9,9a-hexahydro[1]benzopyrano[2,3-c]pyrrole, and its 3aS— and 3aR-isomers; ($\pm$)-trans-8-fluoro-1,2,3,3a,9,9a-hexahydro[1]benzopyrano[2,3-c]pyrrole, and its 3aS— and 3aR— isomers; ($\pm$)-trans-1,2,3,3a,9,9a-hexahydro[1]benzopyrano[2,3-c]pyrrole, and its 3aS— and 3aR-isomers; and their physiologically acceptable salts, particularly the hydrochlorides.

The compounds of the invention have selective $\alpha_2$-adrenoreceptor antagonist action. The test for determining the $\alpha_2$-adrenoreceptor antagonist action is based on the ability to prevent the action of a selective $\alpha_2$-adrenoreceptor agonist such as clonidine or 5-bromo-N-(4,5-dihydro-1H-imidazol-2-yl)-6-quinoxalinamine-[R-(R*R*)]-2,3-dihydroxybutanedioate (UK NO. 14304-18) on the rat field stimulated vas deferense preparation.

Clonidine and UK No. 14304-18 inhibit the twitch response of the rat isolated vas deferense to low frequency motor nerve stimulation. This inhibition is a consequence of activation of presynaptic adrenoreceptors of the $\alpha_2$-type. Antagonism of the effect of clonidine or UK No. 14304-18 is quantified by measuring the parallel shift to the right of the inhibitory $\alpha_2$-adrenoreceptor agonist $\log_{10}$ (concentration)/response curve in the presence of increasing concentrations of the antagonist. Potency and competitiveness of antagonism are determined by the method of Arunlakshana & Schild (Br. J. Pharmac. 1959, 14 48–58).

The $\alpha$-adrenoreceptor-type selectivity of the compounds of general formula (I) is similarly assessed by measuring the ability to produce a parallel shift to the right of the $\log_{10}$ (concentration)/response curve for the $\alpha_1$-adrenoreceptor agonist phenylephrine. The $\alpha_1$-adrenoreceptor-mediated responses of phenylephrine measured were contractions of the rat isolated anococcygeus muscle (Leighton, Butz & Parameter, Eur. J. Pharmac., 1979, 58 27-38).

The compounds of the invention are thus of interest in the treatment or prevention of migraine, thrombosis, diabetes, obesity, hypertension, constipation, paralytic ileus and senile dementia, and in particular for the treatment of depression.

The invention accordingly further provides compounds of general formula (I) and their physiologically acceptable salts for use in the therapy or prophylaxis of migraine, thrombosis, diabetes, obesity, hypertension, constipation, paralytic ileus and senile dementia and in particular depression. The compounds of the invention may be used either alone or with an additional active ingredient. Thus, for example, in the treatment of depression, the compound of the invention may be used alone, or may be co-administered with an established antidepressant (e.g. desmethylimipramine, imipramine or amitriptyline) either in a single formulation or in separate formulations. The established antidepressant can be used in accordance with conventional practice.

The compounds according to the invention may be formulated in a conventional manner, optionally together with one or more other active ingredient, for administration by any convenient route for example for oral, rectal, intravenous or intramuscular administration. Oral administration is preferred.

Thus according to another aspect, the invention provides a pharmaceutical composition comprising a compound of general formula (1) and/or a physiologically acceptable salt thereof together with a physiologically acceptable carrier or excipient. The composition may optionally contain an additional active ingredient, for example an antidepressant such as desmethylimipramine, imipramine or amitriptyline.

For oral administration, the pharmaceutical composition may take the form of, for example, tablets, capsules, powders, solutions, syrups or suspensions prepared by conventional means with physiologically acceptable excipients.

Compositions for rectal administration may be in the form of suppositories using a conventional suppository excipient.

The compounds may be formulated for intravenous or intramuscular administration in dry form for reconstitution before use, or as a sterile solution or suspension.

A proposed daily dose for administration to man is 0.01 to 10 mg/kg, for example 0.05 to 3 mg/kg, which may be conveniently administered in 1 to 3 doses per day. The precise dose administered will of course depend on the age and condition of the patient. The daily dosage may conveniently be administered in the form of dosage units, each unit containing for example 0.01 to 3 mg/kg of active ingredient.

The compounds according to the invention may be prepared by a number of processes. In the following description the groups R, $R^1$ and $R^2$ are as previously defined for general formula (I) except where otherwise indicated.

According to a first example (A), a compound of general formula (I) may be prepared by amination of a compound of general formula (II)

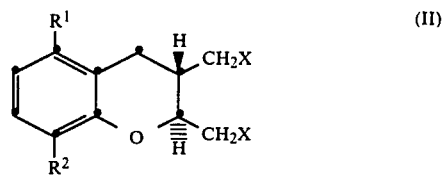

where
X is a leaving group such as a halogen atom, (e.g. chlorine, bromine or iodine), or a hydrocarbylsulphonyloxy group e.g. methylsulphonyloxy,
with ammonia, aqueous ammonia or an amine of formula $RNH_2$ where R is as previously defined except that R is not a hydrogen atom or the group —CHO.

In a particular embodiment of this process, following the amination reaction, the resulting compound of general formula (I) or a salt thereof, may be converted into another compound of general formula (I). Thus, for example, when R is arylmethyl, the amination reaction may optionally be followed by removal of the arylmethyl group to yield a compound of formula (I) where R is a hydrogen atom.

The amination reaction is conveniently effected at an elevated temperature e.g. under reflux or in a sealed tube at e.g. 110° C., preferably in the presence of a suitable base e.g. sodium hydride or an alkali metal hydroxide such as sodium hydroxide or in the presence of an excess of the amine $RNH_2$, optionally in the presence of a solvent such as an ether e.g. dioxan, chlorinated hydrocarbon e.g. chloroform or an alcohol e.g. ethanol. Optional removal of an arylmethyl group may be carried out for example by hydrogenolysis or, where appropriate, under acidic conditions, as described below.

According to another example (B), a compound of general formula (I) where R represents a hydrogen atom may be prepared by deprotection of a corresponding compound where R represents a protecting group. Suitable protecting groups include, for example, arylmethyl and acyl groups. Conventional deprotection procedures may be used. For example, where appropriate an arylmethyl group (e.g. benzyl) may be removed by hydrogenolysis using, for example, hydrogen in the presence of a catalyst, such as platinum or palladium on a support (e.g. charcoal), in a solvent such as an alcohol e.g. methanol. Alternatively, where appropriate, an arylmethyl group (e.g. trityl) may be removed under acidic conditions, using for example an acid such as trifluoroacetic acid, formic acid or hydrobromic acid. Acyl groups may be removed by hydrolysis using an acid such as mineral acid or a base such as an alkali metal hydroxide as appropriate. The protected starting materials for this process may be prepared using standard methods for the protection of amines, for example as described by J. F. W. McOmie in 'Protective Groups in Organic Chemistry' (Plenum Press, 1973).

According to a further example (C), a compound of general formula (I) where R represents an alkyl group may be prepared by reduction of the corresponding compound in which R is an acyl group using a reducing agent such as lithium aluminium hydride or diborane in a suitable solvent such as ether or tetrahydrofuran at an elevated temperature e.g. reflux. Suitable acyl groups are, for example, formyl, acetyl, or carbonyloxyalkyl e.g. carbonyloxymethyl. The intermediate starting materials for this reaction may be prepared by acylation using conventional methods, for example by reaction of the compound of formula (I) in which R represents a hydrogen atom, with an acid chloride, acid anhydride, or ester.

The product of any of the processes (A), (B) and (C) described above may be subjected to one or two further reactions comprising: (D) (i) converting the resulting compound of general formula (I) or a salt thereof into another compound of general formula (I); and/or (D) (ii) converting a compound of general formula (I) or a salt thereof into a physiologically acceptable salt thereof.

Thus, it is also possible to prepare a compound of general formula (I) by a process comprising interconversion of another compound of general formula (I).

For example, a compound of general formula (I) in which R is a hydrogen atom may be converted by alkylation to a compound of general formula (I) in which R is an alkyl, substituted alkyl, alkenyl, alkynyl or aralkyl group. Conventional alkylation procedures may be used, for example reductive alkylation using an appropriate aldehyde with a complex metal hydride such as sodium or potassium borohydride or sodium cyanoborohydride in a suitable solvent such as an alcohol e.g. methanol.

Alternatively, the alkylation may be performed with an alkylating agent RX (where R is an alkyl, substituted alkyl, alkenyl, alkynyl or aralkyl group and X is a leaving group such as a halogen atom e.g. chlorine or bromine, or a hydrocarbylsulphonyloxy group e.g. p-toluenesulphonyloxy) preferably in the presence of a base, such as potassium carbonate, optionally in a solvent such as an alcohol, e.g. ethanol.

Another example of this embodiment is the preparation of a compound of general formula (I) where R is a group —CHO, which may be prepared by formulation of a corresponding compound of formula (I) in which R is a hydrogen atom using an appropriate formylating agent such as a formyl ester, e.g. an alkyl formate such as methyl formate.

Physiologically acceptable salts of the compounds of general formula (I) may be prepared by reacting the free base of formula (I) or a salt thereof with an appropriate acid, such as hydrogen chloride in the presence of a suitable solvent e.g. ethyl acetate, ether or $CH_2Cl_2$ to obtain the desired physiologically acceptable salt.

The intermediate compounds of general formula (II) may be prepared by reaction of a corresponding diol of formula (III)

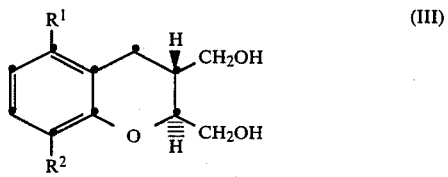
(III)

with a halide of formula $X_1A$ (where $X_1$ is a hydrocarbylsulphonyl group e.g. methylsulphonyl and A is a halogen atom e.g. a chlorine atom) in the presence of a base e.g. triethylamine in a solvent such as dichloromethane; or with a halogenating agent such as thionyl chloride, phosphorous tribromide or hydrogen iodide.

The diols of formula (III) may be prepared by the following sequence of reactions:

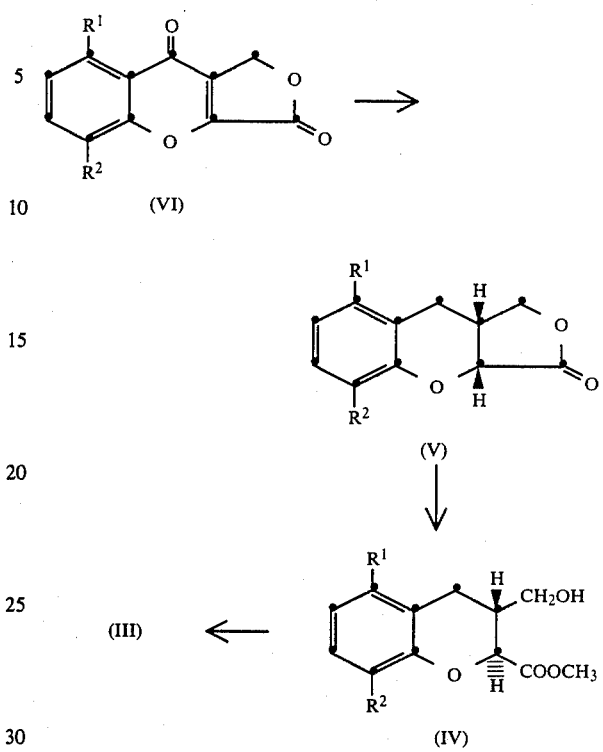

Reduction of the pyrone (VI) using hydrogen and palladium on charcoal in glacial acetic acid yields the lactone (V), which is converted to the ester (IV) by reaction with potassium carbonate and methanol. Reduction of the ester (IV) using lithium aluminium hydride in tetrahydrofuran then gives the required diol (III).

The pyrone of formula (VI) in which $R^1$ and $R^2$ both represent hydrogen is a known compound (Puetzer et al, J. A. C. S. 1945, 67, 832).

The intermediate pyrones of formula (VI) in which one of $R^1$ and $R^2$ represents hydrogen, fluorine or chlorine, and the other represents fluorine or chlorine may be prepared from a compound of formula (VII)

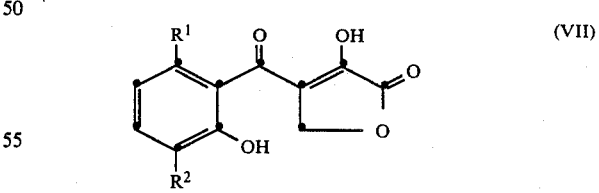
(VII)

(which $R^1$ and $R^2$ are as just defined).

The reaction may be carried out under acidic conditions preferably with heating in a solvent such as glacial acetic acid. Suitable acids for the reaction include mineral acids eg hydrochloric acid or p-toluenesulphonic acid.

The compound (VII) may be prepared from a compound of formula (VIII)

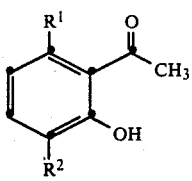

(in which R¹ and R² are as defined in formula (VII)) by reaction with diethyl oxalate in the presence of a strong base such as an alkali metal alkoxide eg sodium ethoxide in a solvent eg an alcohol such as ethanol preferably with heating eg at reflux, followed by reaction of the product formed in situ with aqueous formaldehyde.

Intermediates of formula (VIII) in which R² represents a fluorine or chlorine atom and R¹ represents hydrogen, fluorine or chlorine are either known compounds or can be prepared according to the methods described by J. A. Donnelly and J. J. Murphy, J. Chem. Soc. (C), 1970, 2596–2598.

Intermediates of formula (VIII) in which R² represents hydrogen and R¹ is a fluorine atom may be prepared by the following reaction sequence:

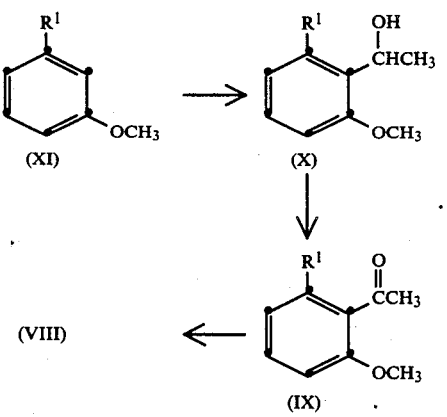

Reaction of the known haloanisole (XI) with a strong base such as n-butyllithium at low temperatures eg −75° C., and subsequent addition of acetaldehyde, yields the compound (X), which is oxidised to the ketone (IX) using a suitable oxidising agent such as pyridinium chlorochromate. Demethylation of the ketone (IX) under standard conditions, eg using boron tribromide in a halohydrocarbon solvent such as dichloromethane provides the required intermediates (VIII).

Intermediate diols of formula (III) in which one of R¹ and R² represents hydrogen or a fluorine or chlorine atom, and the other represents a fluorine or chlorine atom are novel compounds and constitute a further aspect of the present invention.

A specific enantiomer of general formula (I) may be prepared by resolution of a mixture of enantiomers of formula (I) by conventional methods, e.g. by salt formation with an optically active acid followed by separation of the resulting diastereoisomeric salts, e.g. by fractional crystallisation. Alternatively, resolution may be effected at any suitable intermediate stage.

The following examples illustrate the invention. All temperatures are in °C.

Intermediate 1

2-Fluoro-6-methoxy-α-methyl benzenemethanol n-Butyl lithium (3.9 mls of 1.14M in hexane) was added dropwise to a solution of 3-fluoroanisole (0.45 mls) in dry tetrahydrofuran (10 mls) at −75° under nitrogen. The solution was kept at −75° for 1 hour, and then acetaldehyde (0.68 mls) was added dropwise and the mixture allowed to warm up. 2M Hydrochloric acid (20 mls) was added, the mixture was extracted with ether, the organic solution was dried (MgSO₄) and the solvent was evaporated. The product was distilled to give the title compound as an oil (0.4 g). NMR (CDCl₃) δ 7.17 (1H, d of t, 4-H), 6.75–6.6(2H, m, 3-H, 5-H), 5.24(1H, m, CHO—), 3.89(3H, s, OCH₃), 3.27 (1H, d OH), 1.56(3H, d, CH₃).

Intermediate 2

1-(2-Fluoro-6-methoxyphenyl)ethanone

Pyridinium chlorochromate (47 g) was added in portions to a stirred solution of Intermediate 1 (25 g) in dichloromethane (200 mls). After 3 hours, a further 10 g of reagent was added and stirring was continued overnight. The solution was decanted, the residue was washed thoroughly with ether (200 mls), and the combined solutions were washed through a short column of silica gel, using ether as solvent. Evaporation of the solvent gave a liquid (24 g). A portion was distilled to yield 10.4 g of the title ketone. NMR (CDCl₃) δ 7.30 (1H, d of t, 4-H), 6.77–6.65 (2H, m, 3-H, 5-H), 3.85 (3H, s, OCH₃), 2.53 (3H, s, CH₃).

Intermediate 3

1-(2-Fluoro-6-hydroxyphenyl)ethanone

Boron tribromide (7.3 mls) was added to a stirred solution of Intermediate 2 (12.6 g) in dichloromethane (80 mls) at −65°, and the mixture was allowed to warm to 20° over 2 hours. Water (50 mls) was added dropwise to the stirred mixture, while cooling in a water bath. The layers were separated, the aqueous layer was extracted with dichloromethane and the combined organic solutions were dried (phase separating paper) and the solvent was evaporated. The resulting oil was distilled under vacuum to give the title compound as an oil (6.5 g) NMR (CDCl₃) δ 12.71 (1H, s, OH), 7.36 (1H, d of t, 4-H), 6.85–6.4 (2H, m, 3-H, 5-H), 2.69 (3H, d, CH₃).

Intermediate 4

4-[(2-Fluoro-6-hydroxyphenyl)carbonyl]-3-hydroxy-2(5H)-furanone

A solution of Intermediate 3 (14.4 g) and diethyl oxalate (13.9 mls) in ethanol (50 mls) was added dropwise to a solution of sodium ethoxide (from 4.73 g of sodium) in ethanol (200 mls). The stirred suspension was heated at reflux for 4 hours and allowed to cool. The yellow solid was collected, washed with ethanol and dried. A suspension of the product in water (150 mls) was treated with formaldehyde (6.8 mls of 37% in water) and stirred for 4 hours. The suspension was filtered, the filtrate was acidified at 0° to pH 3 with 10M sulphuric acid, and then extracted with chloroform. The aqueous layer was acidified to pH 1, and further extracted with chloroform. The combined chloroform solutions were dried (phase-separating paper) and the solvent was evaporated. The product was recrystallised twice from chloroform yielding the title compound (3.2 g) M.p. 136°–8°.

Intermediate 5

8-Fluoro-1H-Furo[3,4-b][1]benzopyran-3,9-dione

A solution of Intermediate 4 (13.2 g) and concentrated hydrochloric acid (40 mls) in glacial acetic acid (200 mls) was heated at reflux for 1.25 hours and allowed to cool. Half of the solvent was evaporated under reduced pressure, the precipitated solid was collected, washed with acetic acid and dried to yield the title compound (4.9 g). M.p. 224°–226°.

Intermediate 6

Cis-($\pm$)-8-Fluoro-9,9a-dihydro-1H-furo[3,4-b][1]benzopyran-3-(3aH)-one

Intermediate 5 (7.5 g) in ethyl acetate (250 mls) and acetic acid (50 mls) was hydrogenated over 10% palladium on carbon (1.4 g) for 36 hours. The suspension was filtered, the catalyst was extracted with acetic acid and then hot dioxan. The filtrate was evaporated to dryness and the residual solid was hydrogenated further over 10% palladium on carbon (1 g) in 1,4-dioxan (250 mls) and acetic acid (2 mls) for 48 hours. Filtration and evaporation yielded a crude product that was purified by column chromatography to give the required compound (5.3 g). A portion was recrystallised from toluene/cyclohexane to give white crystals of the title compound. M.p. 97°–98°.

Intermediate 7 trans-($\pm$)-5-Fluoro-3,4-dihydro-3-(hydroxymethyl)-2H-1-benzopyran-2-carboxylic acid methyl ester A mixture of Intermediate 6 (4.8 g) and dried potassium carbonate (9.6 g) in dry methanol was stirred vigorously for 24 hours. The suspension was poured into ethyl acetate and water, the mixture was stirred for 20 minutes and the ethyl acetate layer was collected, washed with water and dried (MgSO$_4$). Evaporation of the solvent and purification of the residue by column chromatography gave the title ester as an oil. (1.25 g). NMR (CDCl$_3$) δ 7.06 (1H, q, 7-H), 6.71 (1H, d, 8-H), 6.62 (1H, t, 6-H), 4.84 (1H, d, 2-H), 3.77 (3H, s, CH$_3$), 3.8–3.55 (2H, m, CH$_2$O), 2.81–2.45 (3H, m, 4-H$_2$, 3-H), 1.78 (1H, t, OH).

Intermediate 8 trans-($\pm$)-5-Fluoro-3,4-dihydro-2H-1-benzopyran-2,3-dimethanol

A solution of Intermediate 7 (1,2 g) in dry tetrahydrofuran was added dropwise to a stirred suspension of lithium aluminium hydride (0.4 g) in tetrahydrofuran (20 mls) at 0°. After 3 hours, saturated ammonium chloride solution (5 mls) was added, the solid was filtered off, washed with tetrahydrofuran and the filtrate was evaporated to dryness. Ethyl acetate was added and the solution was washed with brine, dried (MgSO$_4$) and the solvent was evaporated. The resulting gum was triturated with isopropyl ether to yield the title compound (0.41 g). M.p. 99°–101°.

Intermediate 9 trans-($\pm$)-5-Fluoro-3,4-dihydro-2H-1-benzopyran-2,3-dimethanol bis (methanesulphonate)

A solution of methanesulphonyl chloride (0.77 mls) in dichloromethane (10 mls) was added dropwise to a stirred solution of Intermediate 8 (0.96 g) and triethylamine (1.9 mls) in dichloromethane (10 mls) at 0°. After 1 hour the solution was washed successively with 2M hydrochloric, acid and sodium bicarbonate solution. The organic phase was dried (phase separating paper) and the solvent was evaporated. The resulting solid was triturated with ether, and recrystallised from toluene/cyclohexane to give the title compound as white crystals (0.7 g). M.p. 116°–118°.

Intermediate 10

4-[(3-Fluoro-2-hydroxyphenyl)carbonyl]-3-hydroxy-2(5H)-furanone

A solution of 1-(3-fluoro-2-hydroxyphenyl)ethanone (30 g) and diethyl oxalate (31 g) in ethanol (600 mls) was added dropwise to sodium ethoxide (from 9.85 g of sodium) in ethanol (600 mls) and the mixture was stirred and heated at reflux for 2 days. After the mixture had cooled, it was diluted with 60–80 petrol and the solid was collected and dried. A suspension of the product in water (1.2 l) was stirred with formaldehyde (24 mls of 37%) for 1.5 hours. The solid was filtered out, the filtrate was washed with ether, and traces of ether were removed by evaporation under vacuum. The aqueous solution was acidified to pH 3, the precipitate was collected, washed with water and recrystallised from acetone/water to give the title compound as yellow needles (18.7 g). M.p. 194°–208°.

Intermediate 11

5-Fluoro-1H-furo[3,4-b][1]benzopyran-3,9-dione

A solution of Intermediate 10 (24 g) in acetic acid (200 mls) and concentrated hydrochloric acid (40 mls) was heated at reflux for 1 hour. The mixture was allowed to cool, and was concentrated to a volume of 100 mls. Water was added, the precipitate solid was collected, washed with water and dried to yield the title compound. M.p. 164°.

Intermediate 12

Cis-($\pm$)-5-Fluoro-9,9a-Dihydro-1H-furo[3,4-b][1]benzopyran-3(3aH)-one

Intermediate 11 (23 g) in 1,4-dioxan (500 mls) was hydrogenated for 5 days over 10% palladium on carbon (3 g). Acetic acid (10 mls) and a further 0.8 g of catalyst were added, and hydrogenation was continued for a futher 23 hours. The catalyst was filtered off, washed with ethyl acetate and the filtrate was concentrated to a volume of 150 mls. The suspension was filtered, the filtrate was evaporated to dryness, and the resulting gum was purified by chromatography on silica gel to give the title compound as a white solid. M.p. 75.5°–77.5°.

Intermediate 13 trans-($\pm$)-8-Fluoro-3,4-dihydro-3-(hydroxymethyl)-2H-1-benzopyran-2-carboxylic acid methyl ester A mixture of Intermediate 12 (2 g) and dried potassium carbonate (3.9 g) in dry methanol (20 mls) was stirred under nitrogen for 23 hours. Wet ethyl acetate was added, and the mixture was stirred for 20 minutes. Further quantities of ethyl acetate and water were added, the ethyl acetate layer was separated, washed with water, dried (MgSO$_4$) and the solvent was evaporated. The resulting oil (0.58 g) was purified by chromatography on silica gel, yielding the title compound as an oil. NMR (CDCl$_3$) δ 7.0–6.72 (3H, m, aromatic), 4.96 (1H, d, 2-H), 3.87 (3H, s, methyl ester), 3.67 (2H, d, CH$_2$O—), 2.9–2.5 (3H, m, 3-H, 4-H$_2$), 2.15 (1H, Br, OH).

Intermediate 14 trans-(±)-8-Fluoro-3,4-dihydro-2H-1-benzopyran-2,3-dimethanol

A solution of Intermediate 13 (2.2 g) in dry tetrahydrofuran (30 mls) was added dropwise to a stirred suspension of lithium aluminium hydride (0.46 g) in tetrahydrofuran (30 mls) at 0°–5°. After 1 hour, saturated ammonium chloride solution (10 mls) was added, the solid was filtered off and washed with tetrahydrofuran. Evaporation of the combined solutions yielded a gum which was partitioned between ethyl acetate and water. The aqueous layer was evaporated to dryness, the residue was extracted with ethyl acetate and the combined ethyl acetate layers were dried (MgSO$_4$) and the solvent was evaporated. A solution of the product in a small volume of ethyl acetate was diluted with petrol until no more solid precipitated. The solid was collected and dried to yield the title compound (1.5 g), M.p. 111°.

Intermediate 15 trans-(±)-8-Fluoro-3,4-dihydro-2H-1-benzopyran-2,3-dimethaneol, bis (methanesulphonate)

Methanesulphonyl chloride (1.4 g) was added dropwise to a stirred suspension of Intermediate 14 (1.4 g) in dichloromethane containing triethylamine (1.6 g) at 0°–5°. After 1.5 hours the mixture was washed with 2M hydrochloric acid, the acid layer was extracted with dichloromethane, and the combined organic solutions were dried (phase separating paper) and evaporated to dryness. The residue was purified by column chromatography on silica gel to yield the title compound as a gum (2.4 g). NMR (CDCl$_3$) δ 7.0–6.75 (3H, m, aromatics), 4.54 (2H, d, 2-CH$_2$O), 4.42–4.22 (3H, m, 3-CH$_2$O, 2-H), 3.10, 3.05 (6H, s, s, CH$_3$), 3.02–2.76 (2H, m, 4-H$_2$), 2.53 (1H, m, 3-H).

Intermediate 16

(±)-cis-9,9a-Dihydro-1H-furo[3,4-b][1]benzopyran-3-(3aH)-one

A suspension of 1H-furo[3,4-b][1]benzopyran-3,9-dione (6.1 g) in glacial acetic acid (300 ml) was hydrogenated over 10% palladium on charcoal (1 g) until hydrogen uptake ceased. The catalyst was filtered off and the solvent evaporated from the filtrate to give an oil. The oil was dissolved in ethyl acetate and the solution washed with aqueous sodium bicarbonate and brine. The organic layer was separated, dried (MgSO$_4$) and the solvent evaporated. Crystallisation of the residue from ethyl acetate/ether gave the title compound (3.85 g) m.p. 107°–111°.

Intermediate 17

(±)-trans-3,4-Dihydro-3-(hydroxymethyl)-2H-1-benzopyran-2-carboxylic acid, methyl ester To Intermediate 16 (0.19 g) in dry methanol (2 ml) was added anhydrous potassium carbonate (0.41 g), the mixture was stirred at room temperature for two days, then partitioned between ethyl acetate and brine. The organic layer was separated, dried (MgSO$_4$) and the solvent evaporated to give a solid. Recrystallisation from ether/petroleum ether b.p. 60°–80° gave the title compound (0.04 g) m.p. 84°–85°.

Intermediate 18

(±) trans-3,4-Dihydro-2H-1-benzopyran-2,3-dimethanol

A solution of Intermediate 17 (1.4 g) in dry tetrahydrofuran (30 ml) was added to a stirred, ice cooled, mixture of lithium aluminium hydride (0.24 g) and tetrahydrofuran (20 ml) over 0.3 hr. After 1.5 hr a further quantity of lithium aluminium hydride (0.12 g) was added and the mixture was stirred at room temperature. After an additional 1 hr the reaction was cooled to 0°–5° and saturated ammonium chloride solution (10 ml) added dropwise. The mixture was filtered and the gummy solid washed well with tetrahydrofuran. The combined filtrate and washings were evaporated and the residue partitioned between ethyl acetate and brine. The aqueous phase was separated and twice extracted with ethyl acetate. The combined extracts were dried (MgSO$_4$) and the solvent evaporated. The residue was crystallised from ether/petroleum ether b.p. 60°–80° to give the title compound (1.05 g) m.p. 82°–85°.

Intermediate 19

(±)-trans-3,4-Dihydro-2H-1-benzopyran-2,3-dimethanol, bis (methanesulphonate)

To a stirred mixture of Intermediate 18 (1.02 g) and triethylamine (2.25 ml) in dry dichloromethane (25 ml) at 0°–5° was added methanesulphonyl chloride (0.93 ml) in dichloromethane (25 ml) over 15 min. After 20 min the solution was washed successively with water, 2N-hydrochloric acid, saturated sodium bicarbonate solution, and water. The organic phase was separated, dried (MgSO$_4$), and the solvent evaporated. Trituration of the residue with ether gave the title compound (1.67 g) m.p. 96°–98°.

EXAMPLE 1 trans-(±)-8-Fluoro-1,2,3,3a,9,9a-hexahydro-2-(phenylmethyl)-[1]benzopyrano[2,3-c]pyrrole A mixture of Intermediate 9 (0.63 g) and benzylamine (0.93 mls) was heated at 120° under nitrogen for 45 minutes. Water (10 mls) was added to the cold mixture to give a solid which was collected, washed with water and dried to give the title compound (0.43 g). NMR (CDCl$_3$) δ 7.4–7.2 (5H, m, Ph), 7.06 (1H, q, 6-H), 6.7–6.58 (2H, m, 5-H, 7-H), 4.05 (1H, d of t, 3a-H), 3.88 3.79 (2H, ABq, CH$_2$Ph), 3.18, 3.0 (each 2H, t, 1-H$_2$, 3-H$_2$), 2.67–2.42 (2H, m, 9-H$_2$), 2.29 (1H, m, 9a-H).

EXAMPLE 2 trans-(±)-8-Fluoro-1,2,3,3a,9,9a-hexahydro[1]benzopyrano[2,3-c]pyrrole hydrochloride A solution of Example 1 (0.42 g) in methanol (10 mls) was treated with excess hydrogen chloride in methanol and the solution was evaporated to dryness. The residue was redissolved in methanol and was hydrogenated over 10% palladium on charcoal (50 mg) at 40°–50° until reaction was complete. The solvent was evaporated, the product was treated with hydrogen chloride in ethanol, evaporated to dryness and the solid was triturated with isopropyl alcohol to give the title compound (0.25 g). M.p. 220°–2°. NMR (DMSOd$_6$) δ 9.72 (2H, Br-s, NH$_2^+$), 7.22 (1H, q, 6-H), 6.9–6.7 (2H, m, 5-H, 7-H), 4.21 (1H, d of t, 3a-H), 3.78–2.6 (6H, m, 3-H$_2$, 1-H$_2$, 9-H$_2$), 2.22 (1H, m, 9a-H).

EXAMPLE 3 trans-($\pm$)-5-Fluoro-1,2,3,3a,9,9a-hexahydro-2-(phenylmethyl)-[1]benzopyrano[2,3-c]pyrrole, hydrochloride A mixture of benzylamine (6.7 g) and Intermediate 15 (2.3 g) was stirred and heated to 120° under nitrogen for 50 minutes. After cooling, the mixture was partitioned between ethyl acetate and 2M sodium hydroxide solution, the layers were separated and the aqueous layer was further extracted with ethyl acetate. The combined organic solutions were washed with brine and then shaken with 2M hydrochloric acid. The precipitated solid was collected, washed with water and ethyl acetate, and dried to give the title compound as a white powder (1.3 g). M.p. 210°–212°. NMR (DMSOd$_6$) $\delta$ 12.28, 12.00 (1H, 2×Br S, NH+), 7.8–7.6, 7.6–7.4 (5H, m, Ph), 7.2–6.85 (3H, m, 7-H, 6-H, 8-H), 4.65–4.1 (3H, m, C$\underline{H}_2$Ph, 3a-H), 3.9–2.25 (7H, m, 1-H$_2$, 3-H$_2$, 9-H$_2$ 9a-H).

EXAMPLE 4 trans-($\pm$)-5-Fluoro-1,2,3,3a,9,9a-hexahydro[1]benzopyrano[2,3-c]pyrrole hydrochloride A solution of Example 3 (1.2 g) in methanol (50 mls) was hydrogenated over 10% palladium on charcoal (0.2 g) for 17 hours. The catalyst was filtered off, and the filtrate was evaporated to dryness. Crystallisation of the resulting solid from isopropyl alcohol/methanol gave the title compound (0.63 g). M.p. 259°. NMR (DMSOd$_6$) $\delta$ 9.9 (2H, Br S, NH$_2$+), 7.2–6.85 (3H, m, aromatic), 4.24 (1H, d of t, 3a-H), 3.8–2.78 (6H, m, 1-H$_2$, 3-H$_2$, 9-H$_2$), 2.27 (1H, m, 9a-H).

EXAMPLE 5

($\pm$)-trans-1,2,3,3a,9,9a-Hexahydro-2-(phenylmethyl)[1]-benzopyrano[2,3-c]pyrrole Intermediate 19 (1.49 g) and benzylamine (2.32 ml) were mixed and heated to 120° under nitrogen for 45 min. Water (10 ml) was added to the cold mixture to give a white solid, which was filtered off, washed with cold water and dried in vacuo over P$_2$O$_5$ to give the title compound (1.11 g), m.p. 68°–70°, NMR (CDCl$_3$) $\tau$ 2.6–2.85 (5H, m, phenyl), 2.85–3.3 (4H, multiplets, aromatic), 5.96 (1H, m, 3a-H), 6.15 and 6.24 (2H, ABq, J12,C$\underline{H}_2$Ph), 6.8–7.5 (6H, multiplets, 1-H$_2$, 3-H$_2$, and 9-H$_2$), and 7.67 (1H, m, 9a-H).

EXAMPLE 6

($\pm$)-trans-1,2,3,3a,9,9a-Hexahydro[1]benzopyrano[2,3-c]-pyrrole, hydrochloride To the compound of Example 5 (1.09 g) in methanol (40 ml) was added 10.9M hydrogen chloride in methanol (0.41 ml) and 10% palladium on charcoal (0.1 g). The mixture was hydrogenated at 50° until hydrogen uptake ceased. The catalyst was removed by filtration and the filtrate evaporated to give a white solid. Recrystallisation from propan-1-ol gave the title compound (0.56 g) m.p. darkens from 225° and melts 265°–270° (d), NMR (DMSO-d$_6$) $\tau$ 2.7–3.2 (4H, multiplets, aromatic), 5.85 (1H, m, 3a-H), 6.2–6.5 and 6.8–7.3 (6H, multiplets, 1-H$_2$, 3-H$_2$ and 9-H$_2$), and 7.77 (1H, m, 9a-H).

Pharmaceutical Examples

In the following examples, 'Active Ingredient' refers more particularly to ($\pm$)-trans-1,2,3,3a,9,9a-hexahydro[1]benzopyrano [2,3-c]pyrrole hydrochloride or ($\pm$)-trans-5-fluoro-1,2,3,3a,9,9a-hexahydro[1]benzopyrano[2,3-c]pyrrole hydrochloride. Other compounds of the invention may be formulated in similar fashion.

1. Oral Capsule

|  | per capsule |
|---|---|
| Active Ingredient | 50 mg |
| Magnesium stearate | 0.5 mg |
| Anhydrous lactose | 50 mg |

Blend the active ingredient with the lactose and magnesium stearate. Fill the blend into appropriate size hard gelatin capsules (lock fitting type) on an automatic capsule filling machine).

2. Oral Syrup

|  | per 5 ml dose |
|---|---|
| Active Ingredient | 50 mg |
| Sodium citrate | 25 mg |
| Citric acid | to pH 4.5 |
| Sunset yellow FCF (Dye) | 0.25 mg |
| Methyl hydroxybenzoate sodium | 5.0 mg |
| Propyl hydroxybenzoate sodium | 2.0 mg |
| Liquid orange flavour | qS |
| Sucrose | 3.25 g |
| Purified water | to 5.0 ml |

Dissolve the sucrose in a minimum quantity of water. Add a concentrated solution of sodium citrate with stirring and adjust the pH to 4.5 with citric acid. With continued stirring, add a 10% aqueous solution of the active ingredient, followed by a solution of the dye, a solution of the hydroxybenzoates and lastly the flavour. Adjust almost to volume with water and stir. Check the pH and adjust to 4.5 with citric acid if necessary. Make up to volume with water.

3. Oral Tablet

|  | per tablet |
|---|---|
| Active Ingredient | 50 mg |
| Polyvinylpyrrolidone | 4.0 mg |
| Sodium starch glycollate | 10.0 mg |
| Magnesium stearate | 2.0 mg |
| Lactose to tablet core weight to | 200 mg |

Blend the active ingredient with the lactose. Add a sufficient quantity of polyvinylpyrrolidone solution to produce a damp mass suitable for granulation. Prepare the granules and dry using a tray or fluid bed dryer. Pass through a sieve, blend with the remaining ingredients and compress into 8 mm diameter tablets on a tablet machine.

Film coat the tablet cores with hydroxypropyl methyl cellulose or similar film forming material, using either an aqueous or non-aqueous solvent system. A plasticizer and suitable colour may be included in the film coating solution.

We claim:

1. A compound of general formula (I)

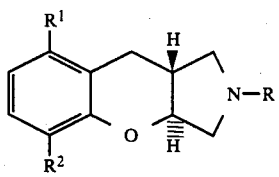 (I)

wherein
R is a hydrogen atom or a group selected from unsubstituted $C_{1-6}$ alkyl, $C_{1-6}$ alkyl substituted with $C_{3-7}$ cycloalkyl, $C_{3-6}$ alkenyl, $C_{3-7}$ cycloalkyl, phen ($C_{1-5}$) alkyl and CHO; and $R^1$ and $R^2$, which may be the same or different, each represents a hydrogen atom or a fluorine or chlorine atom;
and the physiological acceptable salts thereof.

2. A compound according to claim 1, wherein, in the general formula (I), R is a $C_{1-3}$ alkyl group.

3. A compound according to claim 1, wherein in the general formula (I), R is a hydrogen atom.

4. A compound according to claim 1, wherein in the general formula (I) one of $R^1$ and $R^2$ or both of $R^1$ and $R^2$ represent a fluorine atom.

5. A compound selected from (±)-trans-5-fluoro-1,2,3,3a,9,9a-hexahydro[1]benzopyrano[2,3-c]pyrrole, its 3aS— and 3aR-isomers, and their physiologically acceptable salts.

6. A compound selected from (±)-trans-8-fluro-1,2,3,3a,9,9a-hexahydro[1]benzopyrano[2,3-c]pyrrole, and its 3aS— and 3aR-isomers; (±)-trans-1,2,3,3a,9,9a-hexahydro[1]benzopyrano[2,3-c]pyrrole; and its 3aS— and 3aR-isomers; and their physiologically acceptable salts.

7. An alpha$_2$-adrenoreceptor antagonist phamaceutical composition comprising an alpha$_2$-adrenoreceptor antagonist amount of a compound selected from the group consisting of compounds of formula (I), physiologically acceptable salts thereof and their mixtures, according to claim 1, together with physiologically acceptable carriers or excipients.

8. An $\alpha_2$-adrenoreceptor composition according to claim 7 for use in the treatment of depression which also comprises an effective amount of an established antidepressant selected from the group consisting of desmethylimipramine, imipramine and amitriptyline.

9. A method of treating or preventing migrane, depression, thrombosis, diabetes, obesity, hypertension, constipation, paralytic ileus or senile dementia susceptible to amelioration by an alpha$_2$-adrenoreceptor antagonist, which comprises administering an alpha$_2$-adrenoreceptor antagonist amount of a compound selected from the group consisting of compounds of formula (I) according to claim 1, or physiologically acceptable salts thereof and their mixtures.

* * * * *